(12) United States Patent
Cilingiroglu

(10) Patent No.: US 8,560,081 B2
(45) Date of Patent: Oct. 15, 2013

(54) POWER MANAGEMENT TECHNIQUES FOR IMPLANTED STIMULATORS

(75) Inventor: Ugur Cilingiroglu, Istanbul (TR)

(73) Assignee: Yeditepe Universitesi, Istanbul (TR)

( * ) Notice: Subject to any disclaimer, the term of this patent is extended or adjusted under 35 U.S.C. 154(b) by 13 days.

(21) Appl. No.: 13/498,898

(22) PCT Filed: Sep. 29, 2009

(86) PCT No.: PCT/IB2009/054249
§ 371 (c)(1),
(2), (4) Date: Mar. 28, 2012

(87) PCT Pub. No.: WO2011/039562
PCT Pub. Date: Apr. 7, 2011

(65) Prior Publication Data
US 2012/0185018 A1    Jul. 19, 2012

(51) Int. Cl.
*A61N 1/08* (2006.01)
(52) U.S. Cl.
USPC .............. 607/61; 607/7; 607/11; 607/33
(58) Field of Classification Search
USPC .................. 607/7, 11, 16, 33, 61, 65
See application file for complete search history.

(56) References Cited

U.S. PATENT DOCUMENTS

| | | | |
|---|---|---|---|
| 7,295,872 B2 | 11/2007 | Kelly et al. | |
| 7,444,181 B2 | 10/2008 | Shi et al. | |
| 7,519,428 B1 | 4/2009 | Palmer | |
| 8,014,866 B2 * | 9/2011 | Haefner | 607/28 |

OTHER PUBLICATIONS

International Search Report, mailing date of Jul. 12, 2010, for corresponding International Application No. PCT/IB2009/054249.

* cited by examiner

*Primary Examiner* — Carl H Layno
*Assistant Examiner* — Eugene Wu
(74) *Attorney, Agent, or Firm* — Intellectual Property Law Group LLP

(57) ABSTRACT

Power management methods, systems and circuitry are provided for efficiently energizing implanted stimulators. Efficiency is achieved by automatically adjusting the power-supply voltage of the stimulator channel so that the magnitude of the voltage of the current-sink or current-source providing the stimulation current is regulated within a narrow band just above the minimum acceptable level. Adjustment is done once in every cycle of the external high-frequency power source in order to achieve regulation with a very fine time resolution throughout each stimulation period. The power supply voltage is generated and adjusted by rectifying the high-frequency voltage of the secondary coil of a transcutaneous magnetic link by closing and opening a solid-state switch at appropriate times during positive half cycles for a current-sink, and during negative half-cycles for a current-source. The timing of switch closure and opening is dictated by a logic controller on the basis of two binary signals generated by two separate comparators, one of which comparing the voltage of the secondary coil with the generated power-supply voltage, and the other comparing the current-sink or current-source voltage with a reference voltage.

20 Claims, 10 Drawing Sheets

POWER MANAGEMENT TECHNIQUES FOR IMPLANTED STIMULATORS

CROSS-REFERENCE TO RELATED APPLICATIONS

This application is a U.S. National Phase application, under 35 U.S.C. §371, of International Application no. PCT/IB2009/054249, with an international filing date of Sep. 29, 2009, which is hereby incorporated by reference for all purposes.

BACKGROUND

Electrical stimulation of nerves and tissues by implanted stimulators is widely utilized for treating a number of disorders including deafness, blindness, pain and sleep apnea. Stimulation is performed by forcing constant-current pulses between pairs of implanted electrodes in intimate contact with the tissue. Stimulator may contain just one pair of electrodes or a plurality of electrodes, out of which, appropriate pairs are selected for stimulating different localities of tissue in a sequential manner. There exist various different circuit architectures for generating the current pulses and commuting them among electrode pairs. A simplified schematic of one example is shown in FIG. 1. The stimulator contains N electrodes $E_1, E_2, \ldots, E_N$, which, in most cases, are capacitively coupled to the tissue. These electrodes are connectable to a dc power supply source 101 of voltage $V^+$ by means of switches $S_{1A}, S_{2A}, \ldots, S_{NA}$, and to a current sink 102 of stimulation current I by means of switches $S_{1B}, S_{2B}, \ldots, S_{NB}$. Any pair of electrodes can be selected for stimulation by connecting one of the electrodes to the voltage source 101 and the other to the current sink 102. If, for example, electrode $E_1$ is connected to the voltage source 101 and electrode $E_2$ is connected to the current sink 102 by closing $S_{1A}$ and $S_{2B}$, a constant current I set by the current sink 102 enters the tissue at electrode $E_1$ and exits the tissue at electrode $E_2$, and flows in that direction for a prescribed time. It is possible to reverse the direction of current by closing switches $S_{1B}$ and $S_{2A}$ instead of $S_{1A}$ and $S_{2B}$. As a matter of fact, each stimulation event of the selected electrode pair is usually performed in two phases; once with the current flowing in one direction through the electrode pair, and next with the same current flowing in the reverse direction through the same electrode pair. By making the durations of these two phases of stimulation identical, the average charge injected into the tissue is nullified to prevent the occurrence of potentially harmful chemical reactions between the electrodes and tissue. This type of stimulation is commonly known as "biphasic stimulation." If only one of the two phases is applied, then, stimulation is called "monophasic stimulation."

A simplified schematic of an alternative stimulator circuit architecture is shown in FIG. 2. This stimulator differs from that of FIG. 1 in two aspects: (i) the stimulation current I is set by a current source 202 instead of the current sink 102 of FIG. 1, and (ii) a power supply voltage source 201 of negative dc voltage $V^-$ is employed instead of the positive dc voltage $V^+$ of FIG. 1. Otherwise, the structure and operation of this stimulator is essentially identical to that of the stimulator shown in FIG. 1.

In most cases, the energy dissipated in the stimulator circuit of FIG. 1 or FIG. 2 is supplied by a transcutaneous magnetic link. One conventional energy supply circuit is shown in FIG. 3. It contains a magnetic link 31 and a rectifier/filter circuit 32. The external primary coil 301 of the magnetic link is driven with a high-frequency alternating voltage $V_{PC}$ from an external power supply 305. The alternating voltage $V_{SC}$ of the implanted secondary coil 302 is half-wave rectified with a diode 303, and the rectified voltage is filtered with a capacitor 304 to generate the dc power supply voltage $V^+$. More sophisticated cases may involve amplitude doubling of the secondary coil alternating voltage $V_{SC}$, full-wave rectification instead of half wave, and/or post-filter regulation.

FIG. 3 also depicts the stimulation current I sunk from $V^+$ by the current sink 102 via electrodes $E_1$ and $E_2$ in compliance with the stimulator architecture shown in FIG. 1. Total equivalent resistance of the two switches connecting these two electrodes between $V^+$ and current sink 102 (e.g., $S_{1A}$ and $S_{2B}$, or $S_{1B}$ and $S_{2A}$) is represented with R in FIG. 3. Also shown in FIG. 3 is an equivalent load impedance $Z_L$, which represents the combined impedance of (i) the two electrode-tissue interfaces, (ii) the bulk of the stimulated tissue, and (iii) the capacitance of the electrode coupling capacitors.

Notice from FIG. 3 that $V^+$ is the sum of the following three individual voltages: (i) The voltage $V_S$ of the current sink 102, (ii) the voltage $V_L$ of the load impedance $Z_L$, and (iii) the voltage $V_R$ of the total switch resistance R. Among these three voltages, $V_R$ can be made as small as desired by reducing the switch resistance R. $V_S$, on the other hand, should be kept greater than a minimum level acceptable by the current sink 102 for maintaining the constant stimulation current I. This acceptable minimum level, however, can be made as low as several hundred millivolts by proper design. $V_L$, on the other hand, is highly variable because (i) the range in which I is prescribed may be no less than two decades wide, and (ii) $Z_L$ varies not only with time during the duration of stimulation due to its capacitive components but also from one electrode pair to another depending on the condition of the electrode-tissue interfaces and the condition of the tissue itself. In cochlear stimulators, for example, the prescribed value of I may vary between tens of microamps and several milliamps, while $Z_L$ may vary from less than a kilohm up to a ten kilohm or so. Therefore, $V_L$ may be anywhere within the range between ten millivolts and ten volts.

For proper operation of the stimulator, the power supply voltage $V^+$ must be set to accommodate even the highest end of this wide range of $V_L$. Otherwise, whenever a maximum $V_L$ is demanded, $V_S$ will drop below the acceptable minimum needed by the current sink 102 for providing the prescribed stimulation current. If, on the other hand, $V^+$ is set to be sufficiently high to accommodate the maximum expected $V_L$, then, under typical conditions of much lesser $V_L$, $V_S$ will rise much above the acceptable minimum level needed by the current sink 102. This will result in unnecessary waste of energy on the current sink 102. For a numerical illustration of this undesirable outcome, consider an example in which the expected maximum load impedance ($Z_L$) is 10 k$\Omega$ and the maximum expected stimulation current (I) is 1 mA. Therefore, the maximum expected value of $V_L$ is 10 V. Assuming a negligible switch resistance (R) and a minimum acceptable $V_S$ of 1 V for proper current-sink operation, $V^+$ should be set to 11 V to cover this worst-case situation. But then, if a load impedance of 1 k$\Omega$ is stimulated with a current of 1 mA, $V_L$ will fall to 1 V, and $V_S$ will rise to 10 V. The current sink will then operate with a voltage excess of 9 V leading to a waste power of 9(V)×1 (mA)=9 mW.

Methods of minimizing the waste of energy on the current source or sink of a nerve stimulator are disclosed in a number of patents. U.S. Pat. No. 7,295,872 issued Nov. 13, 2007 in the name of inventors Shawn Kelly et. al., for example, discloses a technique of replacing the current source/sink circuitry with a voltage source whose voltage varies with time in such a way that the desired constant current is maintained through the electrodes. Unfortunately, the viability of this technique depends on a quantitatively accurate knowledge of the load impedance, which is almost never available due to the uncertainties associated with the electrical properties of the electrode-tissue interface and of the current path through the tissue.

U.S. Pat. No. 7,444,181 issued Oct. 28, 2008 in the name of inventors Jess Weigian et. al., discloses a technique of measuring the voltage of the current source or sink once in a stimulation period and making adjustments to the power supply voltage to minimize the voltage of the current source or sink. Measured voltage is assessed by a microcontroller to determine whether the power supply voltage should be decremented or incremented in fixed steps. Due to a lack of continuous control of the power supply voltage during stimulation period, however, adjustment has to be made for the largest value of the load impedance observed in each stimulation period. This can result in excessive loss of energy during the early part of a stimulation period when load impedance is relatively small. Also, the technique necessitates a complex hardware to implement its algorithmic prescriptions. Furthermore, the voltage regulator used for adjusting the power supply voltage can potentially consume the energy saved from the current source/sink.

U.S. Pat. No. 7,519,428 issued Apr. 14, 2009 in the name of inventor Logan P. Palmer, teaches a technique by which electrodes can operate from two separate power-supply voltages, one being twice as large as the other. Electrodes with sufficiently small load voltage are supplied from the smaller of these voltages, while the others are supplied from the larger voltage. Energy consumption is halved whenever the former group of electrodes are stimulated, but this does not necessarily imply a minimized consumption. Furthermore, a priori knowledge of the maximum load voltage is needed for each electrode individually for correct power-supply voltage assignment.

SUMMARY OF THE INVENTION

The present invention provides power management methods, systems and circuitry for energizing the stimulator channels with a dedicated power-supply voltage adjusted automatically once in every high-frequency cycle throughout each stimulation period to regulate the magnitude of the current-sink or current-source voltage within a narrow band just above the minimum acceptable level for the current sink or source to sustain the demanded stimulation current. The term "stimulation channel," as used herein, refers to the electrical path comprising (i) the current source or sink by which a stimulation current is forced through a pair of electrodes, (ii) said pair of electrodes, and if present, their coupling capacitors, (iii) switches by which said pair of electrodes are selected and connected between the power supply voltage and the current source or sink, and (iv) the tissue situated in between said pair of electrodes.

Since the duration of even the shortest stimulation pulse is no shorter than a hundred or so high-frequency cycles, regulation of the current-sink or current-source voltage is accomplished with a very fine time resolution. While the current-sink or current-source voltage is thus regulated independently of the value of stimulation current or load and switch impedances, power supply voltage automatically adjusts itself in each high-frequency cycle to be the sum of (i) load and switch voltages, and (ii) current-sink or current-source voltage whose magnitude is thus minimized. Unnecessary energy loss on the current sink or current source is thus eliminated.

The present invention can be practiced in any of the two architectures shown in FIG. 1 and FIG. 2, respectively. It can be practiced also in variants of these architectures, where, for example, each stimulation channel has a separate current sink or source. Also, it is applicable in monophasic or biphasic stimulation.

The power-supply voltage is obtained by rectifying the high-frequency alternating voltage of the secondary coil of a transcutaneous magnetic link, and is stored across a filtering capacitor. Rectification and automatic adjustment of the power-supply voltage is accomplished by closing and opening a solid-state switch between the secondary coil and capacitor at appropriate times during positive half cycles for a current-sink, and during negative half-cycles for a current-source. The timing of switch closure and opening is dictated by a logic controller on the basis of two binary signals generated by two separate comparators, first of which compares the high-frequency alternating voltage of the secondary coil with the generated power-supply voltage, and the second compares the current-sink or current-source voltage with a reference voltage. The leading and trailing edges of the binary signal of the former of these two comparators identify the instants of the high-frequency alternating voltage of the secondary coil crossing over or under the generated power-supply voltage in each high-frequency cycle. If switch closure is needed in any given high-frequency cycle, the logic controller initiates it at the appropriate one of these two instants when the voltage across the switch vanishes. Thus the energy consumed on the switch is minimized. Whether a switch closure is needed or not in a given high-frequency cycle is determined by the logic controller from the prevailing level of the binary signal generated by the second comparator. The switch is closed if the current-sink or current-source voltage is less than the reference voltage, otherwise it is kept open for the entire duration of the high-frequency cycle. Adjustment of the power-supply voltage is deemed complete when the current-sink or current-source voltage exceeds the reference voltage. The logic controller opens the switch at that particular instant of the high-frequency cycle. If adjustment has not been completed before the instant voltage across the switch vanishes again, the switch is nevertheless opened at that instant in order not to start discharging the capacitor.

BRIEF DESCRIPTION OF THE DRAWINGS

The above and other aspects, features and benefits of the present invention will be more apparent from the following more particular description thereof, presented in conjunction with the following drawings wherein.

DETAILED DESCRIPTION OF THE INVENTION

Figure 1:
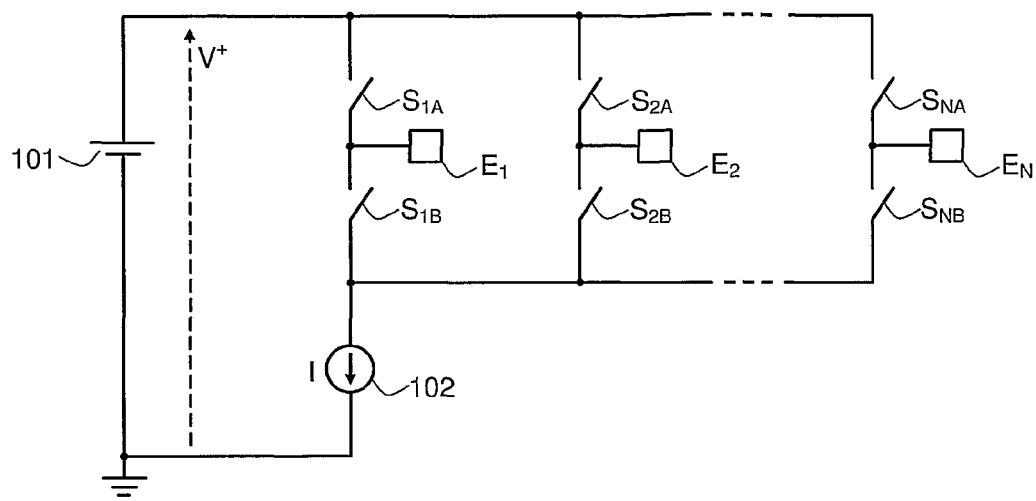
FIG. 1 shows the circuit architecture of an implanted stimulator equipped with a positive power-supply voltage and a current sink (prior art)
Figure 4:
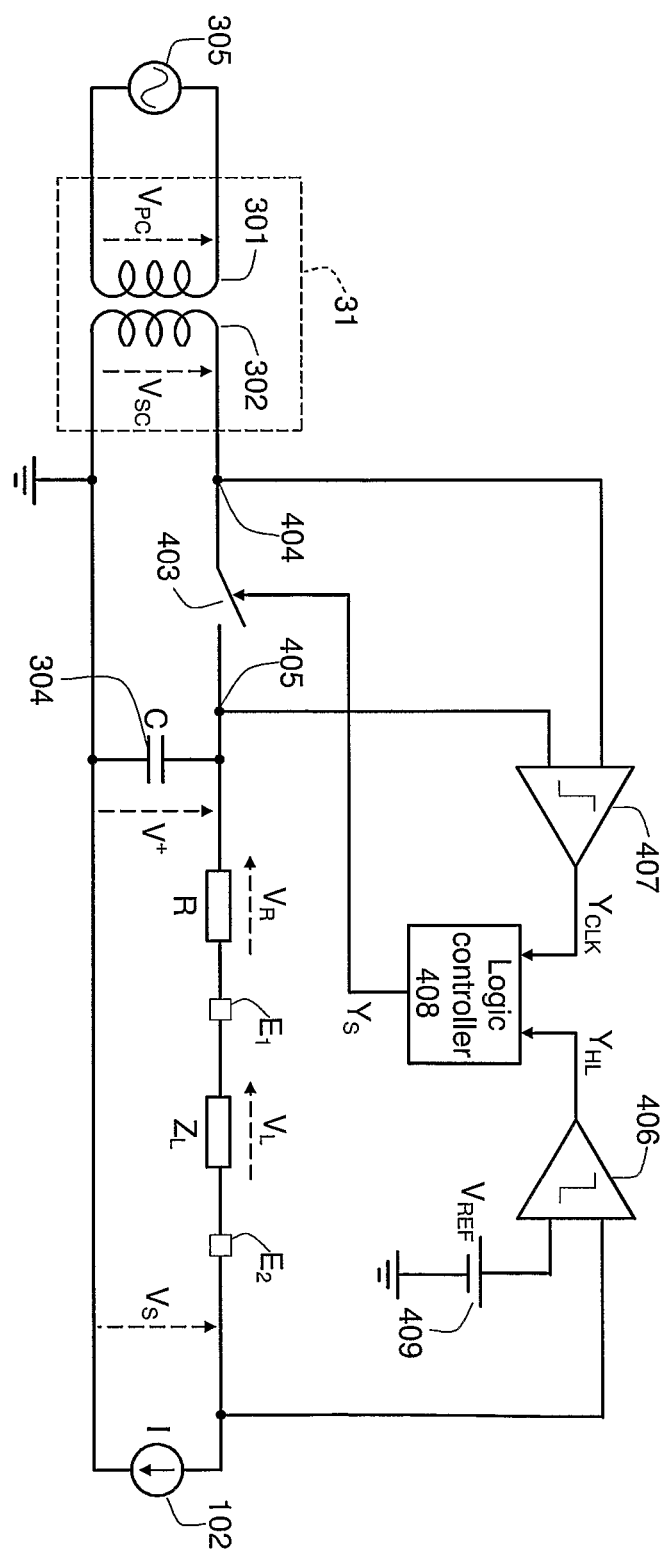
FIG. 4 shows, in accordance with the present methods, systems and circuits, a schematic diagram of power management for a stimulation channel operating with a positive power-supply voltage and a current sink.

Shown in FIG. 4 is an exemplary embodiment of the disclosed power management method as applied to a stimulation channel of the architecture of FIG. 1. The external primary coil 301 of a transcutaneous magnetic link 31 is driven with a high-frequency sinusoidal voltage $V_{PC}$ from an external power supply 305. The sinusoidal voltage $V_{SC}$ of the implanted secondary coil 302 is half-wave rectified by turning on and off a switch 403 between nodes 404 and 405 at appropriate times, and the rectified voltage is filtered with a capacitor 304 of capacitance C to generate a positive power-supply voltage $V^+$. Optionally, a second capacitor can be connected in parallel with the secondary coil so that the capacitance of this second capacitor and the inductance of the secondary coil form a resonant tank circuit, which helps increase the amplitude of $V_{SC}$. Selection of a sinusoidal waveform for $V_{PC}$, and hence for $V_{SC}$, is for illustrative purposes only; other alternating waveforms of gradually rising and falling edges (e.g., triangular waveform) can also be employed. It is also possible to double or triple the amplitude of $V_{SC}$ prior to rectification.

FIG. 4 also depicts a stimulation current I being sunk from $V^+$ by the current sink 102 via electrodes $E_1$ and $E_2$. Total equivalent resistance of the two switches connecting these electrodes between $V^+$ and current sink 102 in the architecture of FIG. 1 (e.g., $S_{1A}$ and $S_{2B}$, or $S_{1B}$ and $S_{2A}$) is represented with R in FIG. 4. Also shown in FIG. 4 is the load impedance $Z_L$, which represents the combined impedance of (i) the two electrode-tissue interfaces at $E_1$ and $E_2$, (ii) the bulk of the stimulated tissue, and (iii) the capacitance of electrode coupling capacitors.

Switch 403 is controlled according to the binary signals generated by the two voltage comparators 406 and 407. Comparator 406 compares the voltage $V_S$ of current-sink 102 with a positive reference voltage $V_{REF}$ provided by the voltage source 409, and generates a binary output signal $Y_{HL}$ whose binary levels represent the cases of $V_S$ being more positive or less positive than $V_{REF}$. $V_{REF}$ is set slightly more positive than the minimum acceptable value of $V_S$ for which the current sink can function properly for the demanded stimulation current. Alternatively, comparator 406 can be replaced with a Schmitt trigger of a small hysteresis range around a built-in reference voltage equivalent to $V_{REF}$. Comparator 407 compares the instantaneous value of the secondary-coil sinusoidal voltage $V_{SC}$ with the power-supply voltage $V^+$, and generates a binary output signal $Y_{CLK}$ whose binary levels represent the cases of $V_{SC}$ being more positive or less positive than $V^+$. $Y_{HL}$ and $Y_{CLK}$ are fed into a logic controller 408, whose binary output signal $Y_S$ opens or closes the switch 403 in each and every high-frequency cycle in accordance with the Rule-1 stated below:

Rule-1: In each high-frequency cycle, sample the output $Y_{HL}$ of comparator 406 at the instant when the output $Y_{CLK}$ of comparator 407 indicates that $V_{SC}$ is crossing over $V^+$, and take one of the following two actions:

Action-1 of Rule-1 If the sampled level of $Y_{HL}$ indicates a $V_S$ less positive than $V_{REF}$, then, close the switch 403, and keep it closed until (i) $V_S$ crosses over $V_{REF}$, or (ii) $V_{SC}$ crosses under $V^+$, whichever comes first. Open the switch 403 when the earlier of these two events occurs, and keep it open until the next instant of sampling.

Action-2 of Rule-1 If the sampled level of $Y_{HL}$ is indicative of $V_S$ being more positive than $V_{REF}$, then, keep switch 403 open until the next instant of sampling.

Figure 5:
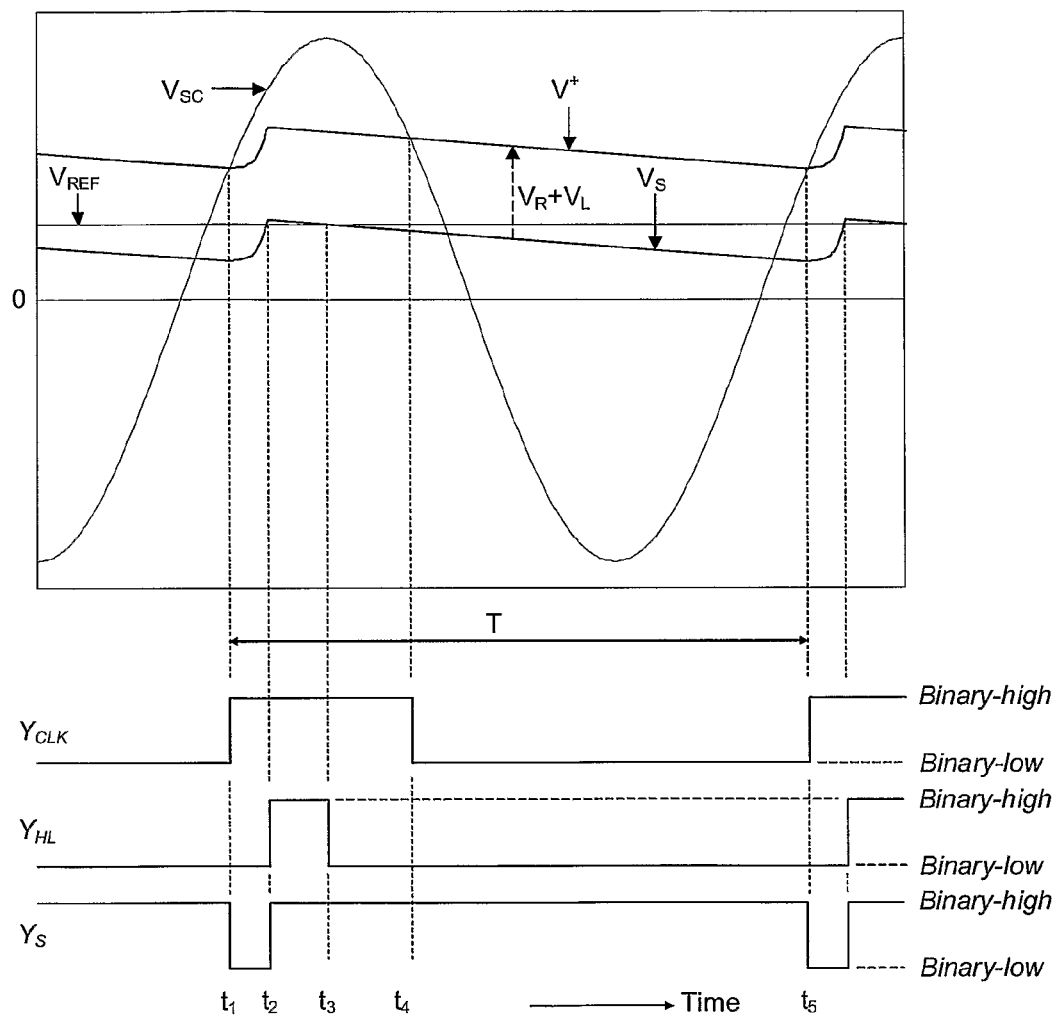
FIG. 5 depicts, in accordance with the present methods, systems and circuits, a set of voltage waveforms exemplifying the periodic steady-state operation of the embodiment shown in FIG. 4, in one of the high-frequency cycles of a stimulation period.

Shown in FIG. 5 is a set of voltage waveforms exemplifying the periodic steady-state operation of the embodiment of FIG. 4 in one of the high-frequency cycles of a stimulation period. For purely illustrative purposes, a binary-high level is assumed to represent (i) the condition $V_{SC} > V^+$ for $V_{CLK}$, and (ii) the condition $V_S > V_{REF}$ for $Y_{HL}$, and a binary-low level is assumed for the condition of switch closure for $Y_S$. Those skilled in the art will appreciate that the logic controller 408 and the switch 403 can be designed to execute Rule-1 also with complementary representations of $Y_{CLK}$, $Y_{HL}$, and $Y_S$.

Execution of the power management method in periodic steady-state can now be explained in conjunction with FIG. 4 and FIG. 5. FIG. 5 shows $V_{SC}$ crossing over $V^+$ at time $t_1$. This event is signalled to logic controller 408 by the comparator 407 raising $Y_{CLK}$ to the binary-high level. At this instant, logic controller 408 samples the output signal $Y_{HL}$ of comparator 406, which signals the condition of $V_S$ being less positive than $V_{REF}$. In compliance with Action-1 of Rule-1, logic controller 408 closes the switch 403 by lowering its output signal $Y_S$ to the binary-low level as fast as it can. The secondary coil 302 now starts charging the capacitor 304 while also supporting the stimulation current I. As a consequence, $V^+$ starts rising. $V_S$, tracking $V^+$, also starts rising. Eventually, at time $t_2$, $V_S$ reaches $V_{REF}$. This event is detected by the comparator 406, which consequently raises its output signal $Y_{HL}$ to the binary-high level. Logic controller 408 responds by also raising its output signal $Y_S$ to the binary-high level, and thus opens the switch 403 in accordance with Action-1 of Rule-1. Due to the nonzero response time of the comparator 406, logic controller 408 and switch 403, however, the instant of switch opening is somewhat delayed with respect to the actual instant of $V_S$ crossing over $V_{REF}$. This delay causes $V_S$ to slightly overshoot $V_{REF}$ before switch 403 is opened. Thereafter, secondary coil 302 is left open, and the stimulation current I starts draining the charge accumulated on the capacitor 304. As a consequence, $V^+$ starts declining at a rate of I/C per unit time until $V_{SC}$ crosses it over again at time $t_5$ of the next high-frequency cycle when logic controller 408 will renew sampling and update $V^+$ in accordance with Rule-1. During the time between $t_2$ and $t_5$, $V_S$ tracks the declining $V^+$ with a difference $V_R + V_L$, where $V_R = I \times R$ and $V_L = I \times Z_L$. This difference remains constant to a very good approximation because the time-constant of the possible variation of $V_R + V_L$ is usually much longer than the time difference between $t_2$ and $t_5$. Therefore, the ripple on $V_S$ (i.e., the total variation of $V_S$ between $t_2$ and $t_5$) is almost the same as the ripple on $V^+$ (i.e., the total variation of $V^+$ between $t_2$ and $t_5$). Assuming that the duration $t_2-t_1$ of the closed state of switch 403 is negligibly short in comparison with the period T of the high-frequency cycle, the common ripple is given approximately by IT/C. By selecting a sufficiently large C, this ripple can be minimized, and thus $V_S$ is stabilized within a narrow band around $V_{REF}$ regardless of the value of I or $Z_L$ or R. Notice that $V_+$ adjusts itself once in each high-frequency cycle to keep $V_S$ regulated within this band around $V_{REF}$ throughout an entire stimulation period. As noted before, $V_{REF}$ is set slightly larger than the minimum voltage needed by the current sink to function properly. Therefore, the current sink 102 consumes the minimum necessary energy at all times while the prescribed stimulation current is successfully sunk independently of load and switch impedances.

For a better understanding of the reasoning behind various aspects of Rule-1, attention is now turned first to the fact that, if switch 403 is to be closed to raise $V^+$ in any high-frequency cycle, closure should not commence before $V_{SC}$ crosses over $V^+$, and should not continue after $V_{SC}$ crosses under $V^+$. This is because switch closure outside this interval would discharge the capacitor 304 instead of charging it. Notice that Action-1 of Rule-1 mandates switch closure right at the beginning of this interval, as exemplified by time $t_1$ and time $t_5$ in FIG. 5, because the energy consumption of switch 403 increases with delay in closure.

Turning attention next to the timing of switch opening, Action-1 of Rule-1 mandates opening at the moment of $V_S$ crossing over $V_{REF}$ if this moment arrives before $V_{SC}$ crosses under $V^+$, as exemplified by time $t_2$ in FIG. 5. This timing is indeed optimum because (i) a later opening would extend $V_S$ far above $V_{REF}$ since charging can continue until $V_{SC}$ crosses under $V^+$, and (ii) an earlier opening would prematurely end the charging process, and thus prevent $V_S$ from reaching $V_{REF}$. In any case, opening of the switch should not be delayed beyond the moment of $V_{SC}$ crossing under $V^+$ in order to avoid discharge. This is why Action-1 of Rule-1 mandates opening at the moment of $V_{SC}$ crossing under $V^+$ even if $V_S$ is still short of $V_{REF}$. This case is unlikely to be encountered in any high-frequency cycle during the periodic steady-state of a stimulation period, and therefore, is not exemplified in FIG. 5, but may be observed in the first few high-frequency cycles of the initial transient state of a stimulation period if a large stimulation current is demanded. A large stimulation current necessitates a large $V^+$, which, in turn, necessitates a large amount of charge to be delivered to the capacitor 304. If such a large charge cannot be completely delivered by the time $V_{SC}$ crosses under $V^+$, $V_S$ enters the next cycle with a value below $V_{REF}$. However, this deficiency is progressively reduced in the following cycles, and thus the steady-state phase of the stimulation period is eventually reached. This case will be further exemplified later in FIG. 7.

Attention is finally turned to the reasoning behind Action-2 of Rule-1. As explained before, the delay in signal propagation through comparator 406, logic controller 408 and switch 403 causes $V_S$ to slightly overshoot $V_{REF}$ before switch 403 is opened. Once the switch has been opened, $V_S$ starts declining, and eventually crosses under $V_{REF}$ again. This is seen to occur at time $t_3$ in the example of FIG. 5. In the case of a weak stimulation current I, however, the rate of decline may be so slow that $V_S$ may remain above $V_{REF}$ at the sampling time of the next high-frequency cycle (e.g., time $t_5$ in FIG. 5). In such a case, Action-2 of Rule-1 keeps switch 403 open for the entirety of the next high-frequency cycle even if $V_S$ crosses under $V_{REF}$ sometime during that next cycle. This prevents switch closure at a time other than the moment of $V_{SC}$ crossing over $V^+$, and thus minimizes the energy consumed by switch 403. This case will be further exemplified later in FIG. 7.

Figure 3:
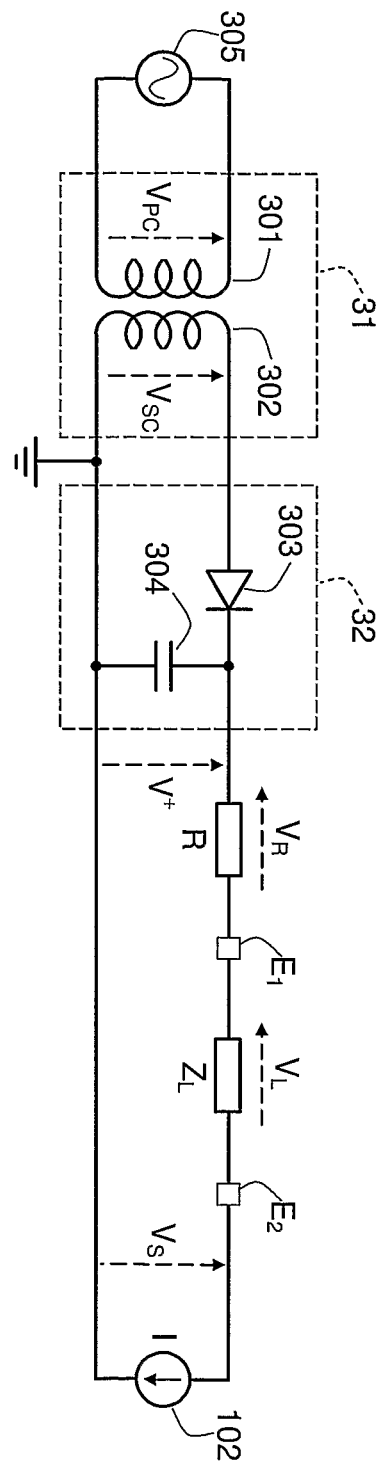
FIG. 3 depicts a schematic diagram of a transcutaneous magnetic link supplying power to a stimulation channel operating with a positive power-supply voltage and a current sink (prior art)

As understood from the description given so far, the circuitry by which the disclosed power management method is applied to the architecture of FIG. 1 comprises the capacitor 304, comparators 406 and 407, the logic controller 408 and the switch 403. These are connected to the rest of the stimulation hardware as per FIG. 4. Except for the capacitor 304, these circuits are preferably integrated on the same chip together with other circuitry needed for performing stimulation. Considering the fact that $V^+$ is variable, a separate constant positive power-supply voltage or a combination of positive and negative power-supply voltages is preferably employed for energizing these circuits as well as other circuits needed for performing the stimulation. These separate power-supply voltages can be generated from the secondary coil 302 with any conventional method such as the one illustrated in FIG. 3.

In regard to the implementation specifics of these circuits, the comparators 406 and 407 can be constructed in any suitable comparator topology known in the art. Switch 403 can be implemented with any suitable solid-state device known in the art, most preferably with a PMOSFET device. Logic controller 408 should be designed as an application specific circuit because it has the specific duty of executing Rule-1.

Figure 6:
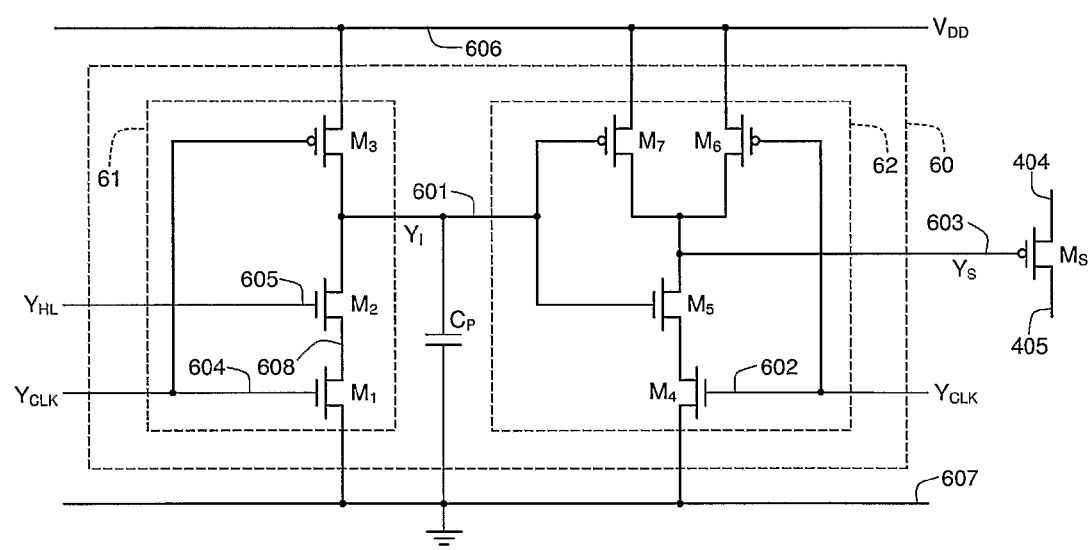
FIG. 6 shows, in accordance with the present methods, systems and circuits, a circuit diagram of one exemplary topology of the logic controller and switch depicted in FIG. 4.

The circuit diagram of one exemplary topology of the logic controller 408 and the switch 403 is shown in FIG. 6. This exemplary topology employs only a positive power-supply voltage $V_{DD}$ applied to node 606, whereas node 607 is connected to the ground. Those skilled in the art will appreciate that an additional negative power-supply voltage can be incorporated by disconnecting node 607 from ground and connecting it to the negative power-supply voltage.

Notice that the PMOSFET device Ms implements the switch 403, whereas the circuit 60 implements the logic controller 408.

The gate terminal of Ms is attached to the output node 603 of the logic controller 60. Node 603 carries the binary switch-control signal $Y_S$ described previously in conjunction with FIG. 4 and FIG. 5. The bulk terminal of $M_S$ (not shown in FIG. 6) is connected to the constant positive power-supply voltage rail $V_{DD}$ at node 606. The remaining two terminals of $M_S$ are connected to node 404 of FIG. 4 and node 405 of FIG. 4, respectively. The propagation delay of the logic controller 60 may be unacceptably long if the gate capacitance of $M_S$ is large. If necessary, this problem can be solved by inserting a non-inverting buffer circuit between the output of the logic controller 60 and the gate of $M_S$ instead of directly interconnecting them as shown in FIG. 6.

Logic controller 60 comprises a dynamic inverter circuit 61 and a static two-input NAND gate 62. The dynamic inverter is built with NMOSFET devices $M_1$ and $M_2$, and PMOSFET device $M_3$. The NAND gate is built with NMOSFET devices $M_4$ and $M_5$, and PMOSFET devices $M_6$ and $M_7$. $C_P$ represents the parasitic capacitance of node 601. Notice that the dynamic inverter 61 drives one of the two inputs of the NAND gate 62 with its output signal $Y_I$ at node 601, whereas the other input of the NAND gate is driven at node 602 by the $Y_{CLK}$ signal described previously in conjunction with FIG. 4 and FIG. 5. One of the inputs of the dynamic inverter 61 receives at node 604 the same $Y_{CLK}$ signal, and the other input receives at node 605 the $Y_{HL}$ signal described previously in conjunction with FIG. 4 and FIG. 5. Node 607 is designated as ground. Note that all NMOSFET devices have their bulk (not shown in FIG. 6) connected to node 607, and all PMOSFET devices have their bulk (not shown in FIG. 6) connected to node 606.

The operation of the logic controller 60 can now be explained with reference to FIG. 4, FIG. 5, and FIG. 6.

Consideration is given first to the case of $Y_{CLK}$ being at ground (i.e., binary-low level). As previously explained, this binary level of $Y_{CLK}$ signals the case of $V_{SC}$ being less positive than $V^+$, for which the switching PMOSFET $M_S$ should be kept open. Indeed, whenever $Y_{CLK}$ is at ground, NAND gate 62 keeps $Y_S$ at $V_{DD}$ (i.e., binary-high level), and therefore $M_S$ remains in cutoff (i.e., open switch state). As to the behavior of the dynamic inverter in the case of $Y_{CLK}$ being at ground, notice that $M_3$ keeps the output signal $Y_I$ of the dynamic inverter at the binary-high level $V_{DD}$ regardless of the binary level of $Y_{HL}$. Therefore, $C_P$ is kept charged to $V_{DD}$ whenever $Y_{CLK}$ is at ground.

Consideration is given next to the case of $Y_{CLK}$ making a transition from ground to $V_{DD}$ while $Y_{HL}$ is at $V_{DD}$. This is the sampling moment when Action-2 of Rule-1 is to be executed. The rising $Y_{CLK}$ forces $M_3$ into cutoff and $M_1$ into conduction, and thus disconnects node 601 from $V_{DD}$, and connects node 608 to ground. Since $M_2$ is also conducting due to $Y_{HL}$ being at $V_{DD}$, $C_P$ is discharged, and hence, $Y_I$ is forced to ground. Now that one of its inputs being lowered to ground, the NAND gate 62 keeps its output $Y_S$ at $V_{DD}$ although its second input receiving $Y_{CLK}$ is raised to $V_{DD}$. $Y_S$ being at $V_{DD}$, $M_S$ retains its cutoff state (i.e., open switch state). Notice that, even if $Y_{HL}$ happens to return later to ground (i.e., $V_S$ crossing under $V_{REF}$) while $Y_{CLK}$ is still at $V_{DD}$ (i.e., $V_{SC}$ being more positive than $V^+$), $M_S$ will continue to be in cutoff because $C_P$ cannot be recharged to $V_{DD}$ before the next falling edge of $Y_{CLK}$. After the arrival of the next falling edge of $Y_{CLK}$, $Y_S$ is kept at $V_{DD}$ anyway, as explained in the preceding paragraph. Therefore, $M_S$ remains in cutoff for the entire cycle if $V_S$ is more positive than $V_{REF}$ at the beginning of the cycle, as mandated by Action-2 of Rule-1.

If $Y_{HL}$ is at the ground level when $Y_{CLK}$ makes a transition from ground to $V_{DD}$, Action-1 of Rule-1 is to be executed. In this case, the rising $Y_{CLK}$ again forces $M_3$ into cutoff and $M_1$ into conduction, and thus disconnects node 601 from $V_{DD}$, and connects node 608 to ground. But, since $Y_{HL}$ is at the ground level, $M_2$ remains in cutoff, and despite the fact that node 608 is connecting the ground, node 601 is left afloat. This enables $C_P$ to retain its charge, and thus to keep $Y_I$ at $V_{DD}$. Now, the NAND gate 62 with both inputs at $V_{DD}$, lowers $Y_S$ to ground, and thus turns $M_S$ on (i.e., closed switch state). If, subsequently, the rising $V_S$ crosses over $V_{REF}$, and therefore, $Y_{HL}$ rises to $V_{DD}$ before $Y_{CLK}$ drops to ground, then, $M_2$ turns on, and together with the conducting $M_1$, discharges $C_P$ to ground. $Y_I$ being lowered to ground, the NAND gate 62 raises $Y_S$ to $V_{DD}$, and thus forces $M_S$ into cutoff (i.e., open switch state). Since $C_P$ cannot be recharged to $V_{DD}$ before the next falling edge of $Y_{CLK}$, $M_S$ remains in cutoff even if $Y_{HL}$ happens to return to ground any time before $Y_{CLK}$ drops to ground. If, on the other hand, $Y_{CLK}$ drops to ground before $Y_{HL}$ rises to $V_{DD}$, then, the NAND gate 62 raises $Y_S$ to $V_{DD}$, and thus forces $M_S$ into cutoff (i.e., open switch state) at the moment $Y_{CLK}$ drops to ground.

Figure 7:
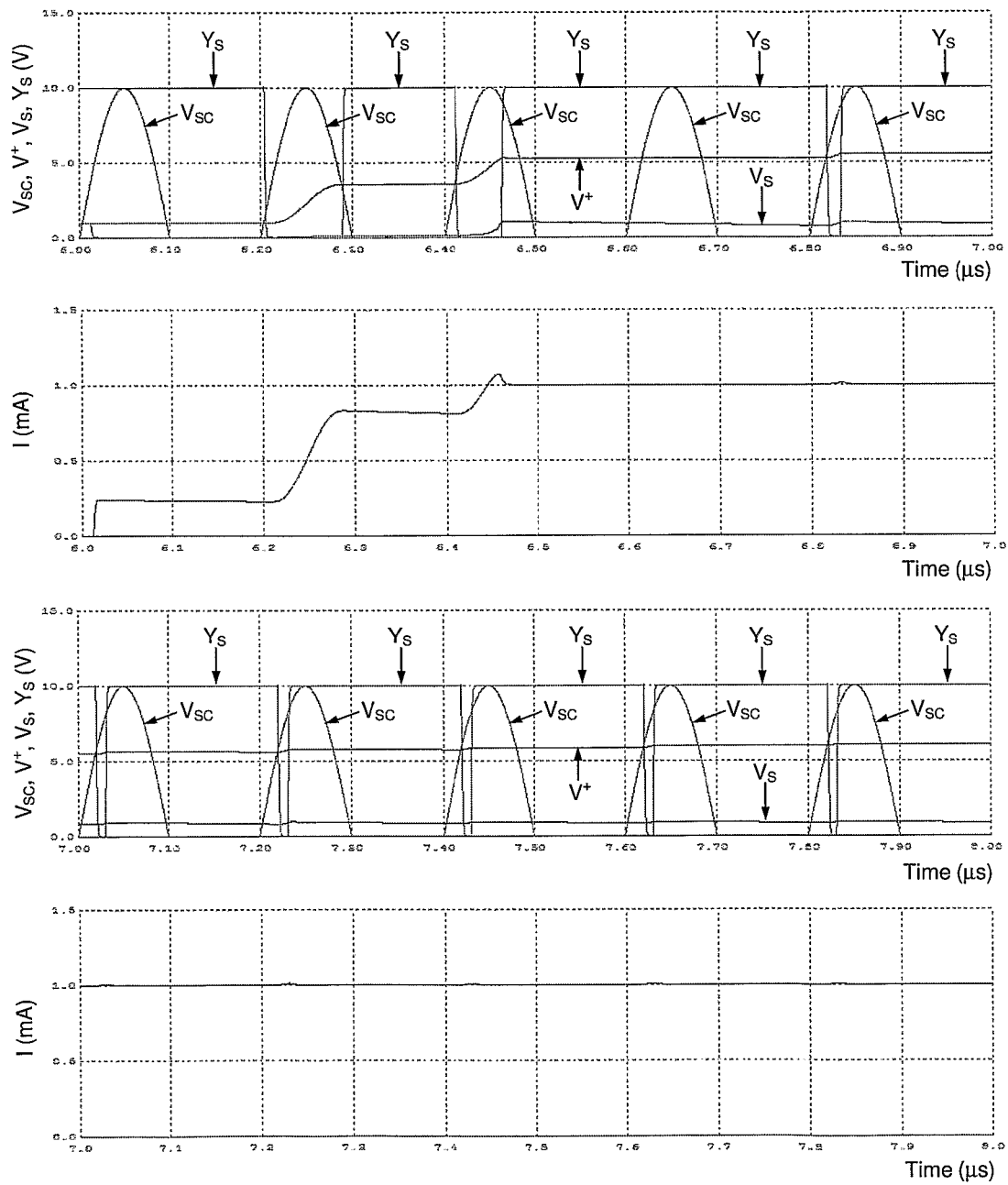
FIG. 7 depicts, in accordance with the present methods, systems and circuits, simulated waveforms representing the transient and steady-state behavior of the embodiment shown in FIG. 4 employing the logic-controller and switch circuit of FIG. 6.

Further illustration of the transient and steady-state behavior of the entire stimulator circuit of FIG. 4 employing the logic-controller and switch circuit of FIG. 6 is provided in FIG. 7 in the form of simulated waveforms. These waveforms belong to the voltages $V_{SC}$, $V^+$, $V_S$, $Y_S$, and the stimulation current I during the first ten 5-MHz cycles of a long stimulation period. Notice that only the positive half cycles of $V_{SC}$ are shown for the sake of brevity. $V_{REF}$ is set to 0.9 V, $V_{DD}$ is set to 10 V, and a stimulation episode is started up shortly after t=6 μs by stepwise demanding 1-mA stimulation current from the current sink. First sampling instant after start-up arrives at the beginning of the second cycle shortly after t=6.2 μs when $V_{SC}$ crosses over $V^+$. Since $V_S$ is smaller than $V_{REF}$ at this instant of sampling, $Y_S$ is lowered to ground, and thus the switch 403 is closed at that instant. Notice that, $V_{SC}$ crosses under $V^+$ in that second cycle while $V_S$ is still considerably short of $V_{REF}$. The switch 403 is nevertheless opened by $Y_S$ raising to $V_{DD}$ in order not to start discharging the capacitor 304. Since $V_S$ is left below the minimum acceptable level for the current sink to function properly, the stimulation current has not reached the demanded level of 1 mA by the end of that second cycle. The switch 403 is again closed when $V_{SC}$ crosses over $V^+$ in the third cycle just after t=6.4 μs, and charging of $V_S$ to $V_{REF}$ is completed before $V_{SC}$ crosses under $V^+$, and therefore, the switch 403 is opened earlier in that third cycle. Notice the absence of switch closure in the fourth cycle starting at t=6.6 μs. This is due to the fact that $V_S$ has somewhat overshot $V_{REF}$ in the previous cycle, and has not declined back to $V_{REF}$ yet at the sampling moment of the fourth cycle. The transient events observed in the second, third and fourth cycles come to an end at the fifth cycle, beyond which the periodic steady-state prevails. In this state, switch closure lasts for a brief interval in each cycle, $V_S$ is stabilized around $V_{REF}$, but $V^+$ continues to rise to accommodate the increasing load impedance.

Figure 2:
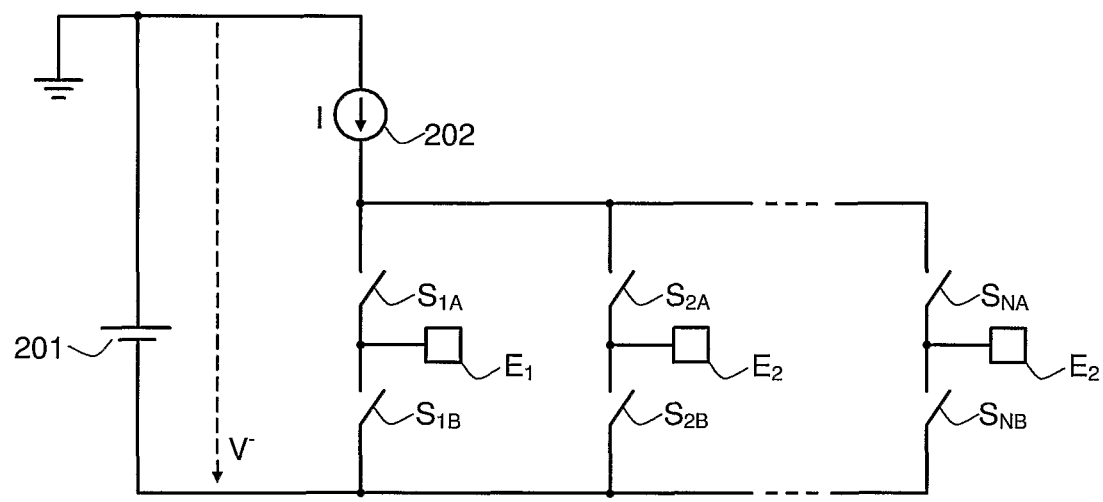
FIG. 2 shows the circuit architecture of an implanted stimulator equipped with a negative power-supply voltage and a current source (prior art)
Figure 8:
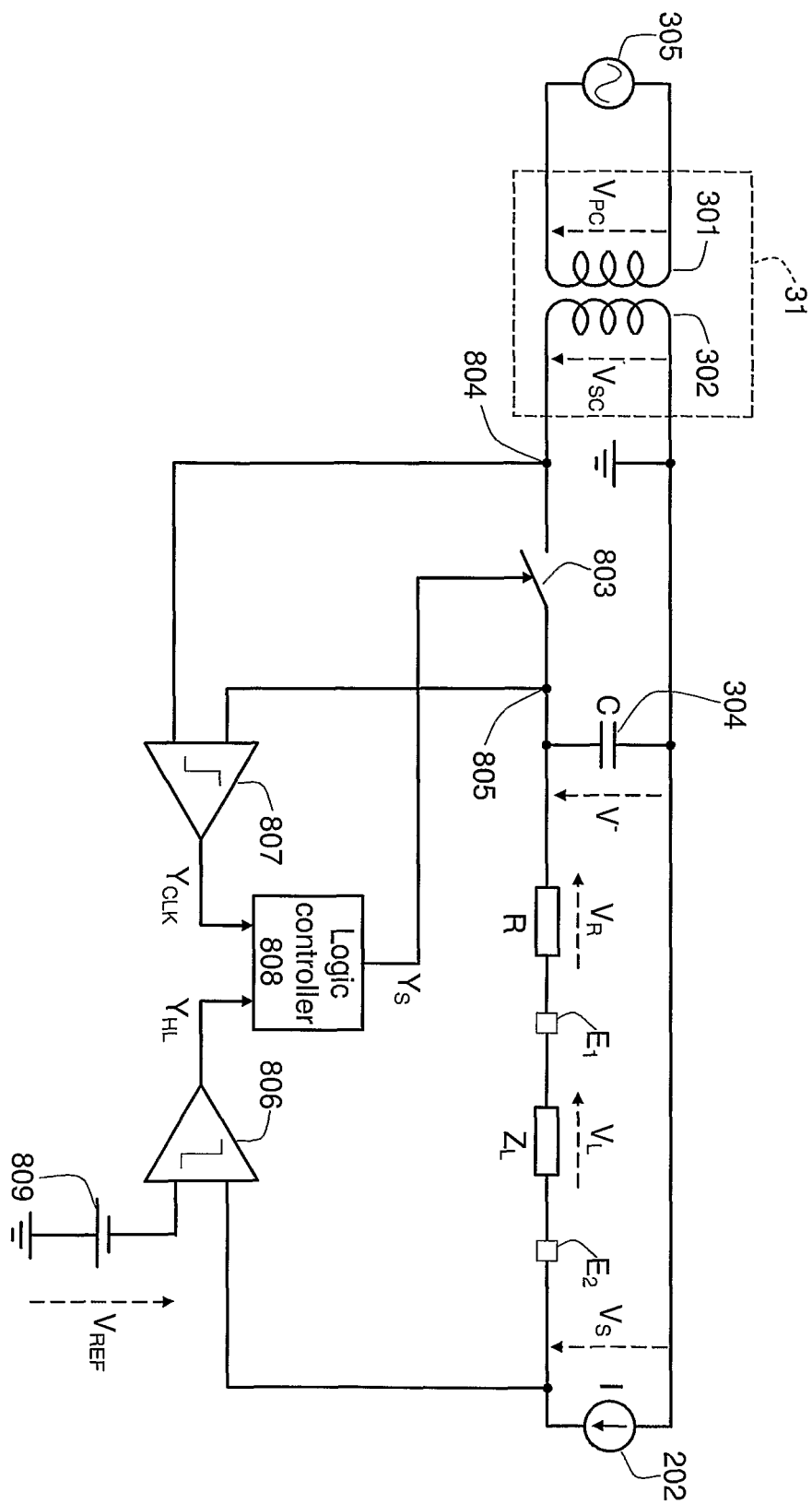
FIG. 8 depicts, in accordance with the present methods, systems and circuits, a schematic diagram of power management for a stimulation channel operating with a negative power-supply voltage and a current source.

The disclosed power management method has so far been described on the embodiment shown in FIG. 4, which is applicable to the stimulation channels of the architecture shown in FIG. 1. A second embodiment of the same method applicable to the stimulation channels of the architecture of FIG. 2 is shown in FIG. 8. A comparison between FIG. 8 and FIG. 4 reveals three differences: (i) Current sink 102 of FIG. 4 is replaced with the current source 202 in FIG. 8, (ii) positive voltage reference 409 of FIG. 4 is replaced with a negative voltage reference 809 in FIG. 8, and (iii) the positive power-supply voltage $V^+$ of FIG. 4 is replaced with a negative power-supply voltage $V^-$ in FIG. 8. The voltages $V_R$, $V_L$, $V_S$ and $V_{REF}$ defined in FIG. 8 are all negative valued.

The duty of comparator 806, comparator 807 and logic controller 808 is essentially the same as the duty of their respective counterparts shown in FIG. 4. These circuits as well as other circuits needed for stimulation are preferably supplied from a separate constant negative power-supply voltage or a pair of negative and positive power-supply voltages, which can be generated from the secondary coil 302 with any conventional method. The rule by which the logic controller rectifies $V_{SC}$ and regulates $V_S$ is based on the same principles as Rule-1 but differs from the latter in the polarity of the conditional statements in order to enable rectification at negative half cycles. The rule is stated below as Rule-2:

Rule-2: In each high-frequency cycle, sample the output $Y_{HL}$ of comparator 806 at the instant when the output $Y_{CLK}$ of comparator 807 indicates that $V_{SC}$ is crossing under $V^-$, and take one of the following two actions:

Action-1 of Rule-2 If the sampled level of $Y_{HL}$ indicates a $V_S$ less negative than $V_{REF}$, then, close the switch 803, and keep it closed until (i) $V_S$ crosses under $V_{REF}$, or (ii) $V_{SC}$ crosses over $V^-$, whichever comes first. Open the switch 803 when the earlier of these two events occurs, and keep it open until the next instant of sampling.

Action-2 of Rule-2 If the sampled level of $Y_{HL}$ is indicative of $V_S$ being more negative than $V_{REF}$, then, keep switch 803 open until the next instant of sampling.

Figure 9:
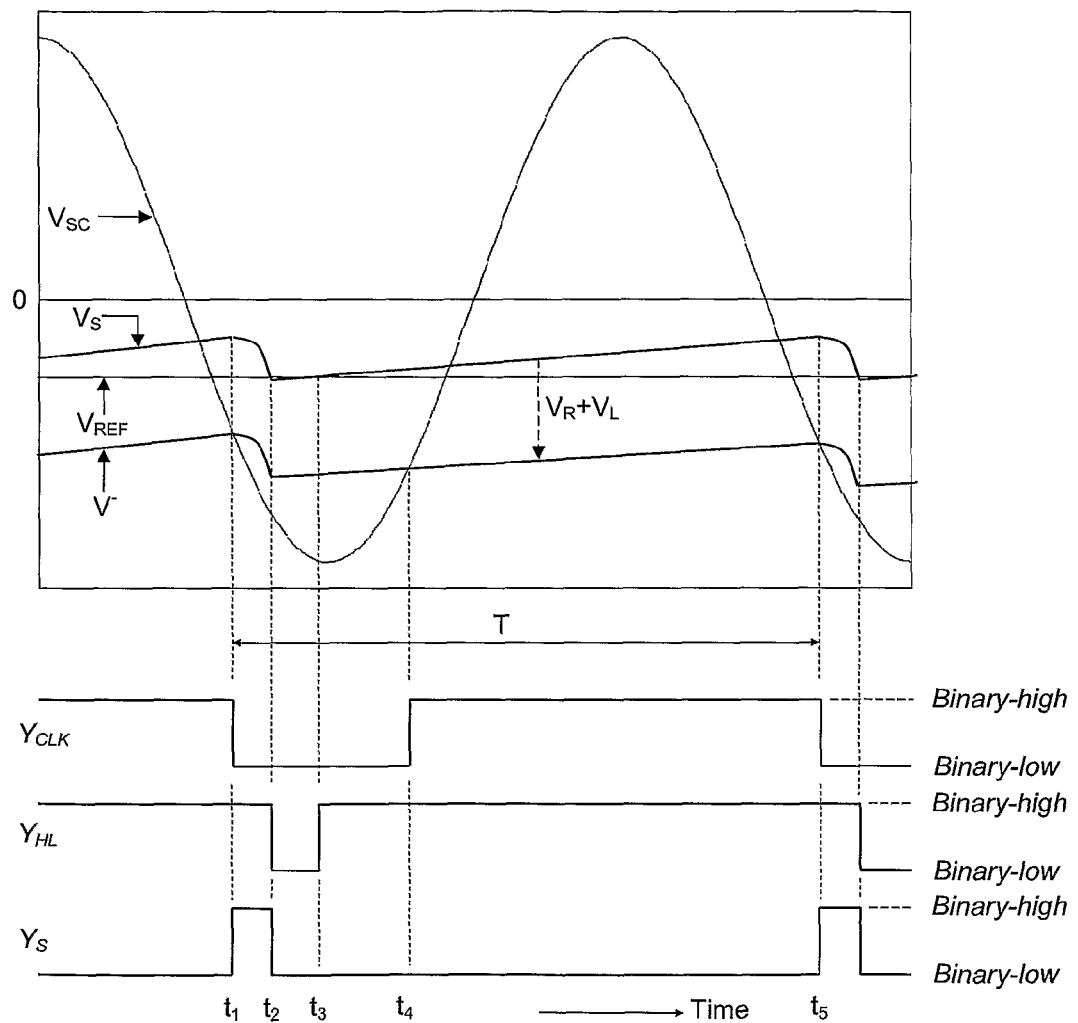
FIG. 9 depicts, in accordance with the present methods, systems and circuits, a set of voltage waveforms exemplifying the periodic steady-state operation of the embodiment shown in FIG. 8, in one of the high-frequency cycles of a stimulation period.

Shown in FIG. 9 is a set of voltage waveforms exemplifying the periodic steady-state operation of the embodiment of FIG. 8 in one of the high-frequency cycles of a stimulation period. For purely illustrative purposes, a binary-low level is assumed to represent (i) the condition $V_{SC}<V^-$ for $Y_{CLK}$, and (ii) the condition $V_S<V_{REF}$ for $Y_{HL}$, and a binary-high level is assumed for the condition of switch closure for $Y_S$. Those skilled in the art will appreciate that the logic controller 808 and the switch 803 can be designed to execute Rule-2 also with complementary representations of $Y_{CLK}$, $Y_{HL}$, and $Y_S$. A person skilled in the art can also interpret the waveforms given in FIG. 9 along the lines of the description given previously for FIG. 5.

In regard to the implementation of the embodiment exemplified in FIG. 8, the comparators 806 and 807 can be constructed in any suitable comparator topology known in the art. Switch 803 can be implemented with any suitable solid-state device known in the art, most preferably with an NMOSFET device. Logic controller 808 should be designed as an application specific circuit because it has the specific duty of executing Rule-2.

Figure 10:
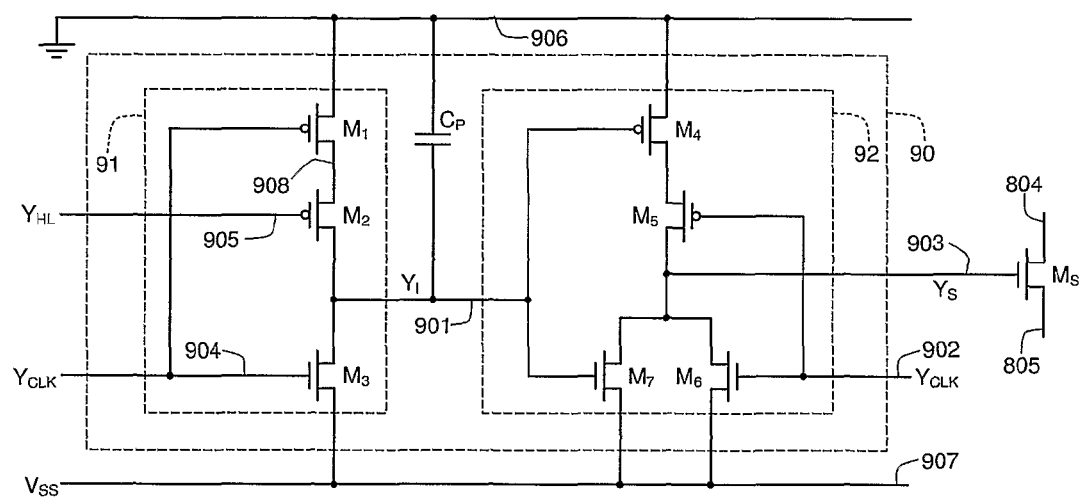
FIG. 10 shows, in accordance with the present methods, systems and circuits, a circuit diagram of one exemplary topology of the logic controller and switch depicted in FIG. 8.

The circuit diagram of one exemplary topology of the logic controller 808 and the switch 803 is given in FIG. 10. This exemplary topology employs only a negative power-supply voltage $V_{SS}$ applied to node 907, whereas node 906 is connected to the ground. Those skilled in the art will appreciate that an additional positive power-supply voltage can be incorporated by disconnecting node 906 from ground and connecting it to the positive power-supply voltage.

Notice that the NMOSFET device $M_S$ implements the switch 803, whereas the circuit 90 implements the logic controller 808.

The gate terminal of $M_S$ is attached to the output node 903 of the logic controller 90. Node 903 carries the binary switch-control signal $Y_S$ previously described in conjunction with FIG. 8 and exemplified in FIG. 9. The bulk terminal of $M_S$ (not shown in FIG. 10) is connected to the constant negative power-supply voltage $V_{SS}$ at node 907. The remaining two terminals of $M_S$ are connected to node 804 of FIG. 8 and node 805 of FIG. 8, respectively. The propagation delay of the logic controller 90 may be unacceptably long if the gate capacitance of $M_S$ is large. If necessary, this problem can be solved by inserting a non-inverting buffer circuit between the output of the logic controller 90 and the gate of $M_S$ instead of directly interconnecting them as in FIG. 10.

Logic controller 90 comprises a dynamic inverter circuit 91 and a static two-input NOR gate 92. The dynamic inverter is built with PMOSFET devices $M_1$ and $M_2$, and NMOSFET device $M_3$. The NOR gate is built with PMOSFET devices $M_4$ and $M_5$, and NMOSFET devices $M_6$ and $M_7$. $C_P$ represents the parasitic capacitance of node 901. Notice that the dynamic inverter 91 drives one of the two inputs of the NOR gate 92 with its output signal $Y_I$ at node 901, whereas the other input of the NOR gate is driven at node 902 by the $Y_{CLK}$ signal described previously in conjunction with FIG. 8 and exemplified in FIG. 9. One of the inputs of the dynamic inverter 91 receives at node 904 the same $Y_{CLK}$ signal, and the other input receives at node 905 the $Y_{HL}$ signal previously described in conjunction with FIG. 8 and exemplified in FIG. 9. Node 906 is designated as ground. Note that all NMOSFET devices have their bulk (not shown in FIG. 10) connected to node 907, and all PMOSFET devices have their bulk (not shown in FIG. 10) connected to node 906.

The operation of the logic controller 90 can now be explained with reference to FIG. 8, FIG. 9, and FIG. 10.

Consideration is given first to the case of $Y_{CLK}$ being at ground (i.e., binary-high level). As previously explained, this binary level of $Y_{CLK}$ signals the case of $V_{SC}$ being less negative than $V^+$, for which the switching NMOSFET $M_S$ should be kept open. Indeed, whenever $Y_{CLK}$ is at ground, NOR gate 92 keeps $Y_S$ at $V_{SS}$ (i.e., binary-low level), and therefore $M_S$ remains in cutoff (i.e., open switch state). As to the behavior of the dynamic inverter in the case of $Y_{CLK}$ being at ground, notice that $M_3$ keeps the output signal $Y_I$ of the dynamic inverter at the binary-low level $V_{SS}$ regardless of the binary level of $Y_{HL}$. Therefore, $C_P$ is kept charged to the negative rail voltage $V_{SS}$ whenever $Y_{CLK}$ is at ground.

Consideration is given next to the case of $Y_{CLK}$ making a transition from ground down to $V_{SS}$ while $Y_{HL}$ is at $V_{SS}$. This is the sampling moment when Action-2 of Rule-2 is to be executed. The falling $Y_{CLK}$ forces $M_3$ into cutoff and $M_1$ into conduction, and thus disconnects node 901 from $V_{SS}$, and connects node 908 to ground. Since $M_2$ is also conducting due to $Y_{HL}$ being at $V_{SS}$, $C_P$ is discharged to ground, i.e., $Y_I$ rises to ground. Now that one of its inputs being raised to ground, the NOR gate 92 keeps its output $Y_S$ at $V_{SS}$ although its second input receiving $Y_{CLK}$ is lowered to $V_{SS}$. $Y_S$ being at $V_{SS}$, $M_S$ retains its cutoff state (i.e., open switch state). Notice that, even if $Y_{HL}$ happens to return later to ground (i.e., $V_S$ crossing over $V_{REF}$) while $Y_{CLK}$ is still at $V_{SS}$ (i.e., $V_{SC}$ is more negative than $V^+$), $M_S$ will continue to be in cutoff because $C_P$ cannot be recharged to $V_{SS}$ before the next rising edge of $Y_{CLK}$. After the arrival of the next rising edge $Y_{CLK}$, $Y_S$ is kept at $V_{SS}$ anyway, as explained in the preceding paragraph. Therefore, $M_S$ remains in cutoff for the entire cycle if $V_S$ is more negative than $V_{REF}$ at the beginning of the cycle, as mandated by Action-2 of Rule-2.

If $Y_{HL}$ is at the ground level when $Y_{CLK}$ makes a transition from ground down to $V_{SS}$, Action-1 of Rule-2 is to be executed. In this case, the falling $Y_{CLK}$ again forces $M_3$ into cutoff and $M_1$ into conduction, and thus disconnects node 901 from $V_{SS}$, and connects node 908 to ground. But, since $Y_{HL}$ is at the ground level, $M_2$ remains in cutoff, and despite the fact that node 908 is connecting the ground, node 901 is left afloat. This enables $C_P$ to retain its charge, and thus to keep $Y_I$ at $V_{SS}$. Now, the NOR gate 92 with both inputs at $V_{SS}$, raises $Y_S$ to ground, and thus turns $M_S$ on (i.e., closed switch state). If, subsequently, the falling $V_S$ crosses under $V_{REF}$, and therefore, $Y_{HL}$ drops to $V_{SS}$ before $Y_{CLK}$ rises to ground, then, $M_2$ turns on, and together with the conducting $M_1$, discharges $C_P$ up to ground. $Y_I$ being raised to ground, the NOR gate 92 lowers $Y_S$ to $V_{SS}$, and thus forces $M_S$ into cutoff (i.e., open switch state). Since $C_P$ cannot be charged to $V_{SS}$ before the next rising edge of $Y_{CLK}$, $M_S$ remains in cutoff even if $Y_{HL}$ happens to return to ground any time before $Y_{CLK}$ rises to ground. If, on the other hand, $Y_{CLK}$ rises to ground before $Y_{HL}$ drops to $V_{SS}$, then, the NOR gate 92 lowers $Y_S$ to $V_{SS}$, and thus forces $M_S$ into cutoff (i.e., open switch state) at the moment $Y_{CLK}$ rises to ground.

What is claimed is:

1. A power management method of generating a positive power-supply voltage from a secondary coil of a transcutaneous magnetic link, and storing said positive power-supply voltage across a capacitor for energizing an implanted stimulator channel, the channel comprising: a current sink by which a stimulation current is forced through a pair of electrodes, said pair of electrodes including their coupling capacitors if incorporated, switches by which said pair of electrodes are selected and connected between said positive power-supply voltage and said current sink;

wherein, said positive power-supply voltage is generated by rectifying an alternating voltage of said secondary coil by closing and opening a solid-state switch between said secondary coil and said capacitor at such times during the positive half of each alternating cycle so that the voltage of said current sink is regulated within a narrow band just above the minimum level needed by said current sink for sustaining the demanded stimulation current;

wherein, said switch is closed at the moment when the alternating voltage of said secondary coil crosses over said positive power-supply voltage if and only if the voltage of said current sink is less positive than a positive reference voltage at that moment;

wherein, said switch is opened at the moment when the voltage of said current sink crosses over said positive reference voltage if the alternating voltage of said secondary coil is more positive than said positive power-supply voltage at that moment;

wherein, said switch is opened at the moment when the voltage of said secondary coil crosses under said positive power-supply voltage if the voltage on said current sink is less positive than said positive reference voltage at that moment; and wherein, said positive reference voltage is set to an appropriate level to confine the voltage of said current sink into said narrow band.

2. A power management method of generating a negative power-supply voltage from a secondary coil of a transcutaneous magnetic link, and storing said negative power-supply voltage across a capacitor for energizing an implanted stimulator channel, the channel comprising: a current source by which stimulation current is forced through a pair of electrodes, said pair of electrodes including their coupling capacitors if incorporated, switches by which said pair of electrodes are selected and connected between said negative power-supply voltage and said current source;

wherein, said negative power-supply voltage is generated by rectifying an alternating voltage of said secondary coil by closing and opening a solid-state switch between said secondary coil and said capacitor at such times during the negative half of each alternating cycle so that the magnitude of the voltage of said current source is regulated within a narrow band just above the minimum level needed by said current source in order to sustain the demanded stimulation current;

wherein, said switch is closed at the moment when the alternating voltage of said secondary coil crosses under said negative power-supply voltage if and only if the voltage of said current source is less negative than a negative reference voltage at that moment;

wherein, said switch is opened at the moment when the voltage of said current source crosses under said negative reference voltage if the alternating voltage of said secondary coil is more negative than said negative power-supply voltage at that moment;

wherein, said switch is opened at the moment when the voltage of said secondary coil crosses over said negative power-supply voltage if the voltage of said current source is less negative than said negative reference voltage at that moment; and wherein, said negative reference voltage is set to an appropriate level to confine the magnitude of the voltage of said current source into said narrow band.

3. A power management system of generating a positive power-supply voltage from a secondary coil of a transcutaneous magnetic link, and storing said positive power-supply voltage across a capacitor for energizing an implanted stimulator channel, the channel comprising: a current sink by which a stimulation current is forced through a pair of electrodes, said pair of electrodes including their coupling capacitors if incorporated, switches by which said pair of electrodes are selected and connected between said positive power-supply voltage and said current sink; the system comprising:

a capacitor, wherein, a first terminal of said capacitor stores said positive power-supply voltage, and a second terminal of said capacitor is connected to the ground of said system together with a first terminal of said secondary coil;

a first voltage comparator comparing a voltage of a second terminal of said secondary coil with said positive power-supply voltage, and putting out a result of comparison with a first binary signal;

a second voltage comparator comparing a voltage of said current sink with a positive reference voltage, and putting out a result of comparison with a second binary signal;

a solid-state switch connected between the second terminal of said secondary coil and the first terminal of said capacitor; wherein, said switch is opened or closed by a third binary signal; and a logic controller receiving said first binary signal and said second binary signal as inputs, and putting out said third binary signal;

wherein, said third binary signal closes said switch at the moment when said first binary signal indicates that an alternating voltage of said secondary coil is crossing over said positive power-supply voltage if and only if said second binary signal indicates that the voltage of said current sink is less positive than said positive reference voltage at that moment;

wherein, said third binary signal opens said switch at the moment when said second binary signal indicates that the voltage of said current sink is crossing over said positive reference voltage, if, at that moment, said first binary signal indicates that the alternating voltage of said secondary coil is more positive than said positive power-supply voltage; and wherein, said third binary signal opens said switch at the moment when said first binary signal indicates that the alternating voltage of said secondary coil is crossing under said positive power-supply voltage if, at that moment, said second binary signal indicates that the voltage of said current sink is less positive than said positive reference voltage.

4. The power management system of claim 3, wherein said second comparator is replaced with a Schmitt trigger.

5. A power management system of generating a negative power-supply voltage from a secondary coil of a transcutaneous magnetic link, and storing said negative power-supply voltage across a capacitor for energizing an implanted stimulator channel, the channel comprising: a current source by which a stimulation current is forced through a pair of electrodes, said pair of electrodes including their coupling capacitors if incorporated, switches by which said pair of electrodes are selected and connected between said negative power-supply voltage and said current source; the system comprising:

a capacitor, wherein, a first terminal of said capacitor stores said negative power-supply voltage, and a second terminal of said capacitor is connected to the ground of said system together with a first terminal of said secondary coil;

a first voltage comparator comparing the voltage of a second terminal of said secondary coil with said negative power-supply voltage, and putting out a result of comparison with a first binary signal;

a second comparator comparing the voltage of said current source with a negative reference voltage, and putting out a result of comparison with a second binary signal;

a solid-state switch connected between the second terminal of said secondary coil and the first terminal of said capacitor; wherein, said switch is opened or closed by a third binary signal; and a logic controller receiving said first binary signal and said second binary signal as inputs, and putting out said third binary signal;

wherein, said third binary signal closes said switch at the moment when said first binary signal indicates that an alternating voltage of said secondary coil is crossing under said negative power-supply voltage if and only if said second signal indicates that the voltage of said current source is less negative than said negative reference voltage at that moment;

wherein, said third binary signal opens said switch at the moment when said second binary signal indicates that the voltage of said current source is crossing under said negative reference voltage, if, at that moment, said first binary signal indicates that the alternating voltage of said secondary coil is more negative than said negative power-supply voltage; and wherein, said third binary signal opens said switch at the moment when said first binary signal indicates that the alternating voltage of said secondary coil is crossing over said negative power-supply voltage if, at that moment, said second binary signal indicates that the voltage of said current source is less negative than said negative reference voltage.

6. The power management system of claim 5, wherein said second comparator is replaced with a Schmitt trigger.

7. A power management circuit of generating a first positive power-supply voltage from a secondary coil of a transcutaneous magnetic link, and storing said first positive power-supply voltage across a capacitor for energizing an implanted stimulator channel, the channel comprising: a current sink by which a stimulation current is forced through a pair of electrodes, said pair of electrodes including their coupling capacitors if incorporated, switches by which said pair of electrodes are selected and connected between said first positive power-supply voltage and said current sink; the circuit comprising:

a capacitor for storing said first positive power-supply voltage; wherein, a first terminal of said capacitor stores said first positive power-supply voltage, and a second terminal of said capacitor is connected to the ground of said power management circuit together with a first terminal of said secondary coil;

a first voltage comparator energized by a second positive power-supply voltage, or by a combination of said second positive power-supply voltage and a negative power supply voltage, and comparing a voltage of a second terminal of said secondary coil with said first positive power-supply voltage, and putting out a result of comparison with a first binary signal;

a second voltage comparator energized by said second positive power-supply voltage, or by a combination of a second positive power-supply voltage and a negative power supply voltage, and comparing a voltage of said current sink with a positive reference voltage, and putting out a result of comparison with a second binary signal;

a PMOSFET device implementing a switch; wherein, a gate terminal receives a third binary signal, a bulk terminal is connected to said second positive power-supply voltage, one of the current conducting terminals is connected to the second terminal of said secondary coil, and the other current conducting terminal is connected to the first terminal of said capacitor; and a binary logic circuit receiving said first binary signal and said second binary signal as inputs, and putting out a third binary signal;

wherein, said third binary signal is lowered to ground or to said negative power-supply voltage at the moment when said first binary signal indicates that an alternating voltage of said secondary coil is crossing over said first positive power-supply voltage if and only if said second binary signal indicates that the voltage of said current sink is less positive than said positive reference voltage at that moment;

wherein, said third binary signal is raised to said second positive power-supply voltage at the moment when said second binary signal indicates that the voltage of said current sink is crossing over said positive reference voltage, if, at that moment, said first binary signal indicates that the alternating voltage of said secondary coil is more positive than said first positive power-supply voltage; and wherein, said third binary signal is raised to said second positive power-supply voltage at the moment when said first binary signal indicates that the alternating voltage of said secondary coil is crossing under said first positive power-supply voltage if, at that moment, said second binary signal indicates that the voltage of said current sink is less positive than said positive reference voltage.

8. The power management circuit of claim 7, wherein said second comparator is replaced with a Schmitt trigger circuit.

9. The power management circuit of claim 8 wherein said third binary signal is passed through a non-inverting buffer circuit before being applied to the gate terminal of said PMOSFET device.

10. The binary logic circuit of claim 8 comprising:

a two-input static CMOS NAND gate energized by said second positive power-supply voltage or by said combination of second positive power-supply voltage and negative power-supply voltage, wherein one of the two inputs receives said first binary signal, and the output voltage represents said third binary signal; and a dynamic CMOS inverter gate, wherein the drain terminal of a first NMOSFET device is connected to the source terminal of a second NMOSFET device; the source terminal of said first NMOSFET device is connected to the ground or to said negative power-supply voltage; the drain terminal of said second NMOSFET device is connected to the drain terminal of a second PMOSFET device; the source of said second PMOSFET device is connected to said second positive power-supply voltage; the interconnected gate terminals of said first NMOSFET device and said second PMOSFET device receives said first binary signal; the gate terminal of said second NMOSFET device receives said second binary signal; the common drain node of said second NMOSFET device and said second PMOSFET device is designated as the output, and is connected to the second input of said two-input static CMOS NAND gate.

11. The power management circuit of claim 7 wherein said third binary signal is passed through a non-inverting buffer circuit before being applied to the gate terminal of said PMOSFET device.

12. The binary logic circuit of claim 11 comprising:

a two-input static CMOS NAND gate energized by said second positive power-supply voltage or by said combination of second positive power-supply voltage and negative power-supply voltage, wherein one of the two inputs receives said first binary signal, and the output voltage represents said third binary signal; and a dynamic CMOS inverter gate, wherein the drain terminal of a first NMOSFET device is connected to the source terminal of a second NMOSFET device; the source terminal of said first NMOSFET device is connected to the ground or to said negative power-supply voltage; the drain terminal of said second NMOSFET device is connected to the drain terminal of a second PMOSFET device; the source of said second PMOSFET device is connected to said second positive power-supply voltage; the interconnected gate terminals of said first NMOSFET device and said second PMOSFET device receives said first binary signal; the gate terminal of said second NMOSFET device receives said second binary signal; the common drain node of said second NMOSFET device and said second PMOSFET device is designated as the output, and is connected to the second input of said two-input static CMOS NAND gate.

13. The binary logic circuit of claim 7 comprising:

a two-input static CMOS NAND gate energized by said second positive power-supply voltage or by said combination of second positive power-supply voltage and negative power-supply voltage, wherein one of the two inputs receives said first binary signal, and the output voltage represents said third binary signal; and a dynamic CMOS inverter gate, wherein the drain terminal of a first NMOSFET device is connected to the source terminal of a second NMOSFET device; the source terminal of said first NMOSFET device is connected to the ground or to said negative power-supply voltage; the drain terminal of said second NMOSFET device is connected to the drain terminal of a second PMOSFET device; the source of said second PMOSFET device is connected to said second positive power-supply voltage; the interconnected gate terminals of said first NMOSFET device and said second PMOSFET device receives said first binary signal; the gate terminal of said second NMOSFET device receives said second binary signal; the common drain node of said second NMOSFET device and said second PMOSFET device is designated as the output, and is connected to the second input of said two-input static CMOS NAND gate.

14. A power management circuit of generating a first negative power-supply voltage from the secondary coil of a transcutaneous magnetic link, and storing said first negative power-supply voltage across a capacitor for energizing an implanted stimulator channel, the channel comprising a current source by which stimulation current is forced through a pair of electrodes, said pair of electrodes including their coupling capacitors if incorporated, switches by which said pair of electrodes are selected and connected between said first negative power-supply voltage and said current source; the circuit comprising:

a capacitor for storing said first negative power-supply voltage; wherein, the first terminal of said capacitor stores said first negative power-supply voltage, and the second terminal of said capacitor is connected to the ground of said power management circuit together with the first terminal of said secondary coil;

a first voltage comparator energized by a second negative power-supply voltage, or by a combination of said second negative power-supply voltage and a positive power-supply voltage, and comparing the voltage of the second terminal of said secondary coil with said first negative power-supply voltage, and putting out the result of comparison with a first binary signal;

a second voltage comparator energized by said second negative power-supply voltage or by a combination of said second negative power-supply voltage and a positive power-supply voltage, and comparing the voltage of said current source with a negative reference voltage, and putting out the result of comparison with a second binary signal;

an NMOSFET device implementing a switch, wherein, gate terminal receives a third binary signal, bulk terminal is connected to said second negative power-supply voltage, one of the current conducting terminals is connected to the second terminal of said secondary coil, and the other current conducting terminal is connected to the first terminal of said capacitor, and a binary logic circuit receiving said first binary signal and said second binary signal as inputs, and putting out a third binary signal;

wherein, said third binary signal is raised to ground or to said positive power-supply voltage at the moment when said first binary signal indicates that the alternating voltage of said secondary coil is crossing under said first negative power-supply voltage if and only if said second binary signal indicates that the voltage of said current source is less negative than said negative reference voltage at that moment;

wherein, said third binary signal is lowered to said second negative power-supply voltage at the moment when said second binary signal indicates that the voltage of said current source is crossing under said negative reference voltage, if, at that moment, said first binary signal indicates that the alternating voltage of said secondary coil is more negative than said first negative power-supply voltage; and wherein, said third binary signal is lowered to said second negative power-supply voltage at the moment when said first binary signal indicates that the alternating voltage of said secondary coil is crossing over said first negative power-supply voltage if, at that moment, said second binary signal indicates that the voltage of said current source is less negative than said negative reference voltage.

15. The power management circuit of claim 14, wherein said second comparator is replaced with a Schmitt trigger circuit.

16. The power management circuit of claim 15, wherein said third binary signal is passed through a non-inverting buffer circuit before being applied to the gate terminal of said NMOSFET device.

17. The binary logic circuit of claim 15 comprising:

a two-input static CMOS NOR gate energized by said second negative power-supply voltage or by said combination of second negative power-supply voltage and positive power-supply voltage, wherein one of the two inputs receives said first binary signal, and the output voltage represents the said third binary signal; and a dynamic CMOS inverter gate, wherein the drain terminal of a first PMOSFET device is connected to the source terminal of a second PMOSFET device; the source terminal of said first PMOSFET device is connected to the ground or to said positive power-supply voltage; the drain terminal of said second PMOSFET device is connected to the drain terminal of an second NMOSFET device; the source of said second NMOSFET device is connected to said second negative power-supply voltage; the interconnected gate terminals of said first PMOSFET device and said second NMOSFET device receives said first binary signal; the gate terminal of said second PMOSFET device receives said second binary signal; the common drain node of said second PMOSFET device and said second NMOSFET device is designated as the output, and is connected to the second input of said two-input static CMOS NOR gate.

18. The power management circuit of claim 14, wherein said third binary signal is passed through a non-inverting buffer circuit before being applied to the gate terminal of said NMOSFET device.

19. The binary logic circuit of claim 18 comprising:
   a two-input static CMOS NOR gate energized by said second negative power-supply voltage or by said combination of second negative power-supply voltage and positive power-supply voltage, wherein one of the two inputs receives said first binary signal, and the output voltage represents the said third binary signal; and
   a dynamic CMOS inverter gate, wherein the drain terminal of a first PMOSFET device is connected to the source terminal of a second PMOSFET device; the source terminal of said first PMOSFET device is connected to the ground or to said positive power-supply voltage; the drain terminal of said second PMOSFET device is connected to the drain terminal of an second NMOSFET device; the source of said second NMOSFET device is connected to said second negative power-supply voltage; the interconnected gate terminals of said first PMOSFET device and said second NMOSFET device receives said first binary signal; the gate terminal of said second PMOSFET device receives said second binary signal; the common drain node of said second PMOSFET device and said second NMOSFET device is designated as the output, and is connected to the second input of said two-input static CMOS NOR gate.

20. The binary logic circuit of claim 14 comprising:
   a two-input static CMOS NOR gate energized by said second negative power-supply voltage or by said combination of second negative power-supply voltage and positive power-supply voltage, wherein one of the two inputs receives said first binary signal, and the output voltage represents the said third binary signal; and
   a dynamic CMOS inverter gate, wherein the drain terminal of a first PMOSFET device is connected to the source terminal of a second PMOSFET device; the source terminal of said first PMOSFET device is connected to the ground or to said positive power-supply voltage; the drain terminal of said second PMOSFET device is connected to the drain terminal of an second NMOSFET device; the source of said second NMOSFET device is connected to said second negative power-supply voltage; the interconnected gate terminals of said first PMOSFET device and said second NMOSFET device receives said first binary signal; the gate terminal of said second PMOSFET device receives said second binary signal; the common drain node of said second PMOSFET device and said second NMOSFET device is designated as the output, and is connected to the second input of said two-input static CMOS NOR gate.

\* \* \* \* \*